(12) United States Patent
Sharifzadeh

(10) Patent No.: US 11,547,331 B1
(45) Date of Patent: Jan. 10, 2023

(54) HYDRATION MONITOR AND METHODS OF USE

(71) Applicant: Mohsen Sharifzadeh, Salt Lake City, UT (US)

(72) Inventor: Mohsen Sharifzadeh, Salt Lake City, UT (US)

( * ) Notice: Subject to any disclaimer, the term of this patent is extended or adjusted under 35 U.S.C. 154(b) by 0 days.

(21) Appl. No.: 15/233,720

(22) Filed: Aug. 10, 2016

Related U.S. Application Data

(60) Provisional application No. 62/203,227, filed on Aug. 10, 2015.

(51) Int. Cl.
| | | |
|---|---|---|
| *A61B 5/1455* | (2006.01) | |
| *A61B 5/00* | (2006.01) | |
| *A61B 5/145* | (2006.01) | |
| *G01N 21/47* | (2006.01) | |
| *G01N 21/31* | (2006.01) | |

(52) U.S. Cl.
CPC ........ *A61B 5/1455* (2013.01); *A61B 5/14546* (2013.01); *A61B 5/443* (2013.01); *A61B 5/4845* (2013.01); *A61B 5/4875* (2013.01); *A61B 5/6824* (2013.01); *A61B 5/6826* (2013.01); *A61B 2562/0238* (2013.01); *G01N 21/31* (2013.01); *G01N 21/4738* (2013.01)

(58) Field of Classification Search
CPC ..... A61B 5/1455; A61B 5/4875; A61B 5/082; A61B 5/7278; A61B 5/443; A61B 2562/0238; G01N 21/31; G01N 21/4738
See application file for complete search history.

(56) References Cited

U.S. PATENT DOCUMENTS

| | | | |
|---|---|---|---|
| 6,750,007 B2 | 6/2004 | Canter et al. | |
| 6,961,598 B2* | 11/2005 | Diab | A61B 5/14532 600/310 |
| 2010/0159611 A1 | 6/2010 | Song et al. | |
| 2011/0288385 A1* | 11/2011 | Stamatas | A61B 5/0059 600/306 |
| 2013/0144136 A1* | 6/2013 | Rymut | A61B 5/0059 600/310 |
| 2013/0261468 A1 | 10/2013 | Semler et al. | |
| 2015/0088431 A1* | 3/2015 | Podhajsky | A61B 5/0059 702/19 |
| 2015/0148623 A1* | 5/2015 | Benaron | A61B 5/0059 600/306 |
| 2015/0223749 A1* | 8/2015 | Park | A61B 5/443 600/473 |
| 2016/0120468 A1* | 5/2016 | Mathew | A61B 5/01 600/301 |

OTHER PUBLICATIONS

Jubran, "Pulse Oximetry," Critical Care (2015), 19:272, 7 pgs.

(Continued)

*Primary Examiner* — Christian Jang
*Assistant Examiner* — Karen E Toth
(74) *Attorney, Agent, or Firm* — Stoel Rives LLP

(57) ABSTRACT

The present disclosure relates to optical methods and devices based on pulsate behavior of blood and optical absorption spectroscopy to measure the level of water and/or other substances or compounds, such as an alcohol or lipid, in the blood and the tissues surrounding blood vessels and arteries.

10 Claims, 8 Drawing Sheets

(56) References Cited

OTHER PUBLICATIONS

Millikan, "The Oximeter, an Instrument for Measuring Continuously the Oxygen Saturation of Arterial Blood in Man," American Institute of Physics, Review of Scientific Instruments (1942), 13, pp. 434-444.
Nitzan et al., "Calibration-Free Pulse Oximetry Based on Two Wavelengths in the Infrared—A Preliminary Study," Sensors (2014), 14, pp. 7420-7434.
Nitzan et al., "Pulse oximetry: fundamentals and technology update," Medical Devices: Evidence and Research (2014), 7, pp. 231-239.

* cited by examiner

HYDRATION MONITOR AND METHODS OF USE

CROSS-REFERENCE TO RELATED APPLICATION

This application claims the benefit of U.S. Provisional Application No. 62/203,227, filed Aug. 10, 2015, which is hereby incorporated by reference in its entirety.

TECHNICAL FIELD

The present disclosure relates generally to the field of medical diagnostic devices, such as devices to quantify hydration status of levels of alcohol or lipids in the plasma of a human subject.

BACKGROUND

Water makes up a substantial portion, both by weight and volume, of the human body. When a body loses more water than it takes in, for example, during exercise or as a result of certain diseases, use of diuretics, or work in high-temperature environments, dehydration may result. As used herein, "dehydration" refers to any condition associated with a lack of body water that is necessary for body functions, including hypernatremia, which is loss of water with an associated increase in plasma sodium concentration, and hypovolemia, which is a decrease in blood volume.

Mild dehydration may cause dizziness and/or fatigue. Even relatively mild cases can impair athletic or work performance. In more severe cases, debilitating physical or mental impairment may result. Severe dehydration may be fatal.

Current methods for assessing a person's hydration status include evaluation of blood or serum levels of certain markers (such as sodium), analysis of urine or saliva, measuring changes in core body temperature, or sending a small electrical current through the skin and measuring the amount of resistance to the current to determine the level of oil and moisture in the tissue.

The present disclosure relates to optical methods and devices based on pulsate behavior of blood and optical absorption spectroscopy to measure the level of water in the blood and the tissues surrounding blood vessels and arteries. This method is not limited to water but may be applied to other substances or compounds in the blood, such as lipids or ethanol. The methods described herein may also be used to determine the bioavailability of other substances or compounds in the blood.

Certain embodiments provide non-invasive, rapid, accurate, repeatable, safe and reliable methods to measure hydration/dehydration in people. To our knowledge, there is not any method to optically measure the level of water in human body. Without being bound by any particular theory, the reason might be the interference of external water, body fluids (like perspiration) and tissue structure (like skin dryness which doesn't relate to body hydration).

The pulsate behavior of blood was used to measure the amount of the water in blood plasma and the neighboring tissue. About half of the human plasma is formed by water, and hydration and dehydration strongly correlate to the amount of water in blood plasma. Using this information, this disclosure provides new methods to directly measure the level of the water in human plasma and obtain the hydration and dehydration status of a subject.

The pulsate behavior of blood could also be used to measure the amount of the alcohol in blood plasma and neighboring tissue. Alcohols (e.g. ethanol) absorb light in the infrared region, and lipid absorbs light in the near infrared region. Excess alcohol in the blood can result in death or an accident. This disclosure provides new methods to directly measure the level of the alcohol in human plasma, which could be used to trigger an alert indicator when a subject's alcohol level exceeds a specified threshold.

The pulsate behavior of blood could also be used to measure the level of lipids and their variation in blood plasma and the neighboring tissue. Lipids have a few absorption bands in the near infrared region. This disclosure provides new methods to directly measure the level and variation of lipids in human plasma, for example after consumption of fatty foods.

The techniques described are similar but not identical to pulse oximetry, which measures oxygen saturation or oxygenation by calculating the difference between two pulse intensities in two different wavelength windows, one that overlaps the deoxyhemoglobin higher absorption band (red region), and one that overlaps the oxyhemoglobin absorption band (NIR region). In these certain embodiments, the amplitudes of two blood pulses, one located in water absorption band and one out of the water absorption band, are compared. This technique could use either a broadband light source which covers red/infrared wavelengths, including both inside and outside the water absorption spectrum, or it could use two narrow band light sources (like light-emitting diodes) in which one light source overlaps the water absorption band and the other is outside of it. Water has four significant absorption bands at approximately 970, 1200, 1450, and 1950 nm. The 970 nm is the strongest detectable band through the blood and tissue, but other absorption bands, or a combination of absorption bands, could be used.

Optical absorption spectroscopy in one of the most common techniques in tissue optics. It compares the incident radiation illuminating a sample with the transmitted or diffused backscattered radiation from the opposite or the same side of the sample. Using Beer-Lambert's law this technique is able to quantify the concentration level of desirable chemical compounds in a tissue sample. But in fact this method alone is not capable of measuring water availability in human tissue due to some external parameters like humidity and external fluids, and internal parameters like human fluids and different tissue characteristics (for example, in dry tissue, light penetration differs from that of normal tissue).

In certain embodiments, the method benefits from using a very low level and completely safe wide-band light source projected, e.g., into a human finger, and then, by comparing the transmitted or diffused backscattered pulse light from the tissue spot in two different wavelength regions, the level of water in blood can be estimated. This level is an indicator of body hydration/dehydration.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in the figures, the figures are not necessarily to scale unless specifically indicated.

Figure 1:
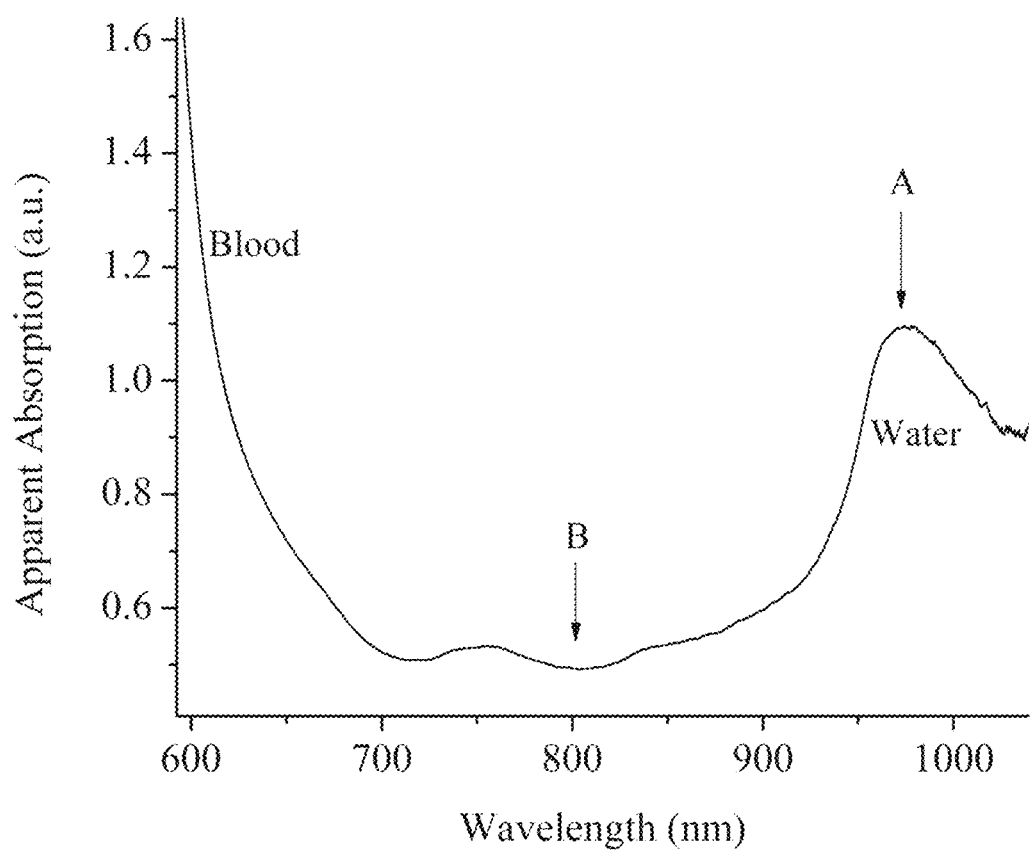
FIG. 1 is an absorption spectrum through a human index finger.

As illustrated in FIG. 1, the absorption spectrum of human tissue (in this case, through an index finger) in the 600-1000 nm wavelength region indicates blood, lipid and water. The main absorption band of water is centered at approximately 970 nm. By comparing the transmitted light or diffused scattered light with illumination light as a reference, it is possible to measure the level of water in tissue, but this measurement is not accurate due to external parameters which strongly affect the measurement. These external parameters include body fluids that contain water (e.g., sweat), ambient water, and tissue structures. By using the pulsate behavior of blood and also tissues closely surrounding blood vessels and arteries, this disclosure provides new methods to measure the level of water in blood regardless of any external parameter.

Figure 2:
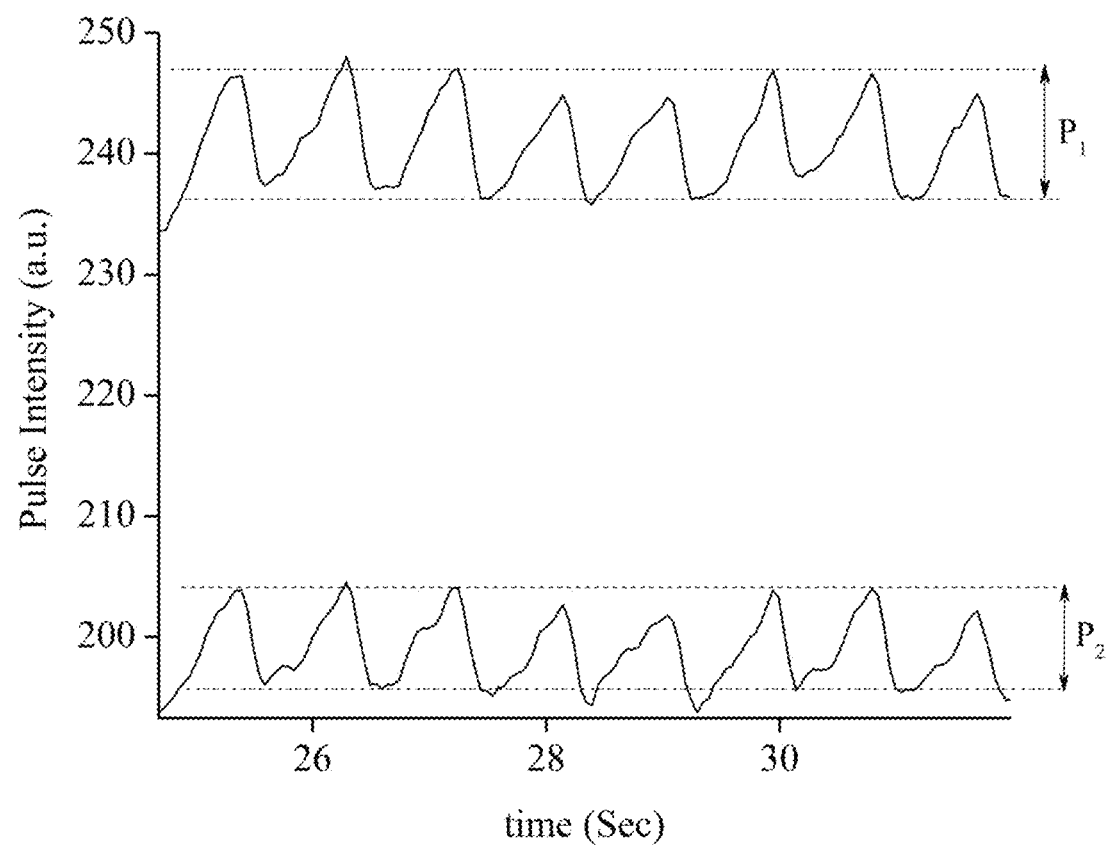
FIG. 2 illustrates the amplitudes of pulsed light in two different wavelength regions.

As indicated in FIG. 2, the amplitude of pulsed light, either transmitted or diffusely scattered, may be determined in two different wavelength regions: one inside the water absorption band (arrow A), and one outside the water absorption band (arrow B). By comparing these two amplitudes, the amount of water in blood may be linearly correlated with the amplitude of the pulse.

In fact this method is not limited to water measurement, as other compounds in the blood can be measured as well (e.g., lipids and ethanol). Lipids, for example, have an optical absorption band at approximately 850 nm. Ethanol has an optical absorption band between 1160-1200 nm. Using these methods, it should be possible to obtain an ethanol level in blood directly and more accurately than using current methods. A device based on this method could be used by health care facilities, law enforcement, etc.

A measurement using this method is illustrated in FIG. 2. The two periodic waveforms in FIG. 2 represent the detected light which is pulsated by blood vessels and arteries. The waveform P1 represents the detected light with 970 nm wavelength, which overlaps the water absorption band, and P2 represents the detected light with 800 nm wavelength, which is outside of water absorption band. It should be noted that the detected light or waveform could be either in absorption or transmission mode. In absorption mode the light passed through the finger is compared to a reference and then converted from transition mode to absorption mode. Comparing the amplitudes of these waveforms gives the water bioavailability or water level in a finger, but the method is not limited to measurements in a finger. Similar measurements can be done using diffused backscattering light to facilitate the measurement in some other part of the body, like the wrist.

Light may be provided by a light source that emits a continuous spectrum (e.g., a halogen-tungsten or tungsten lamp) or by a light-emitting diode (LED) array. The detector may comprise a spectrometer or an array of sensors.

Figure 3:
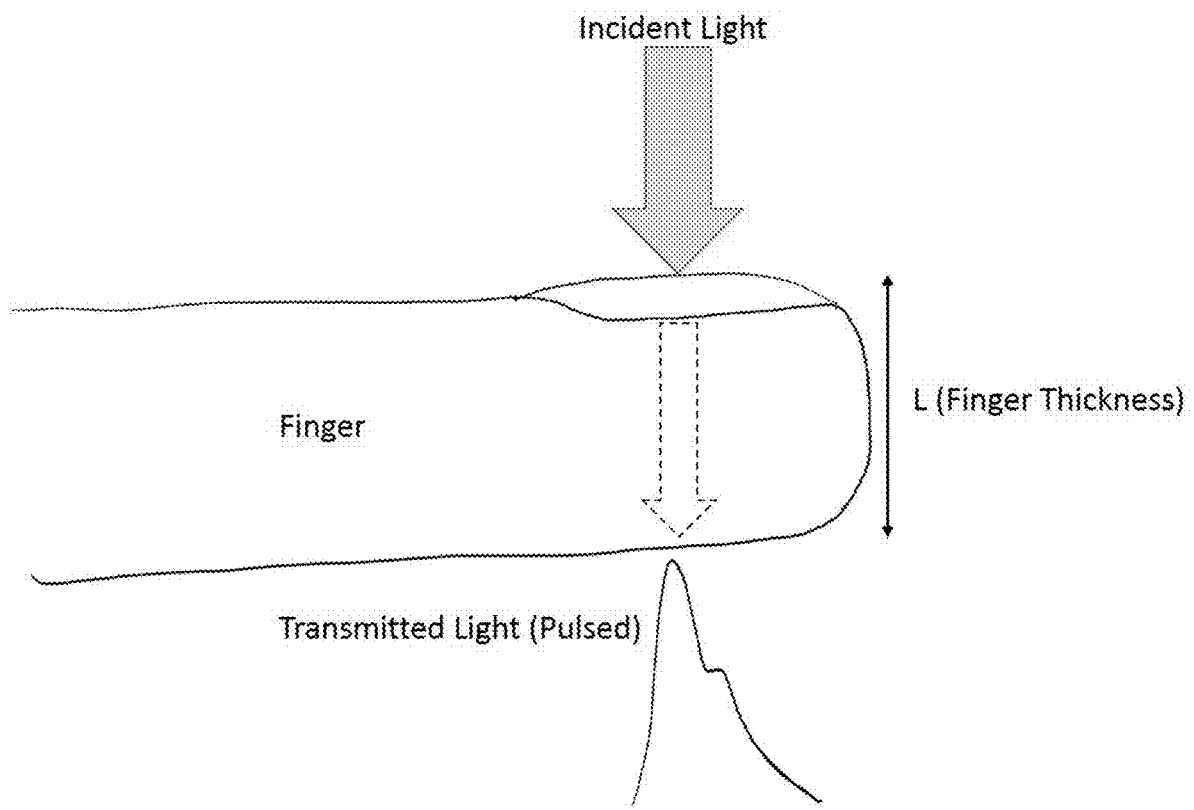
FIG. 3 illustrates the measurement of transmission of light through a finger.
Figure 4:
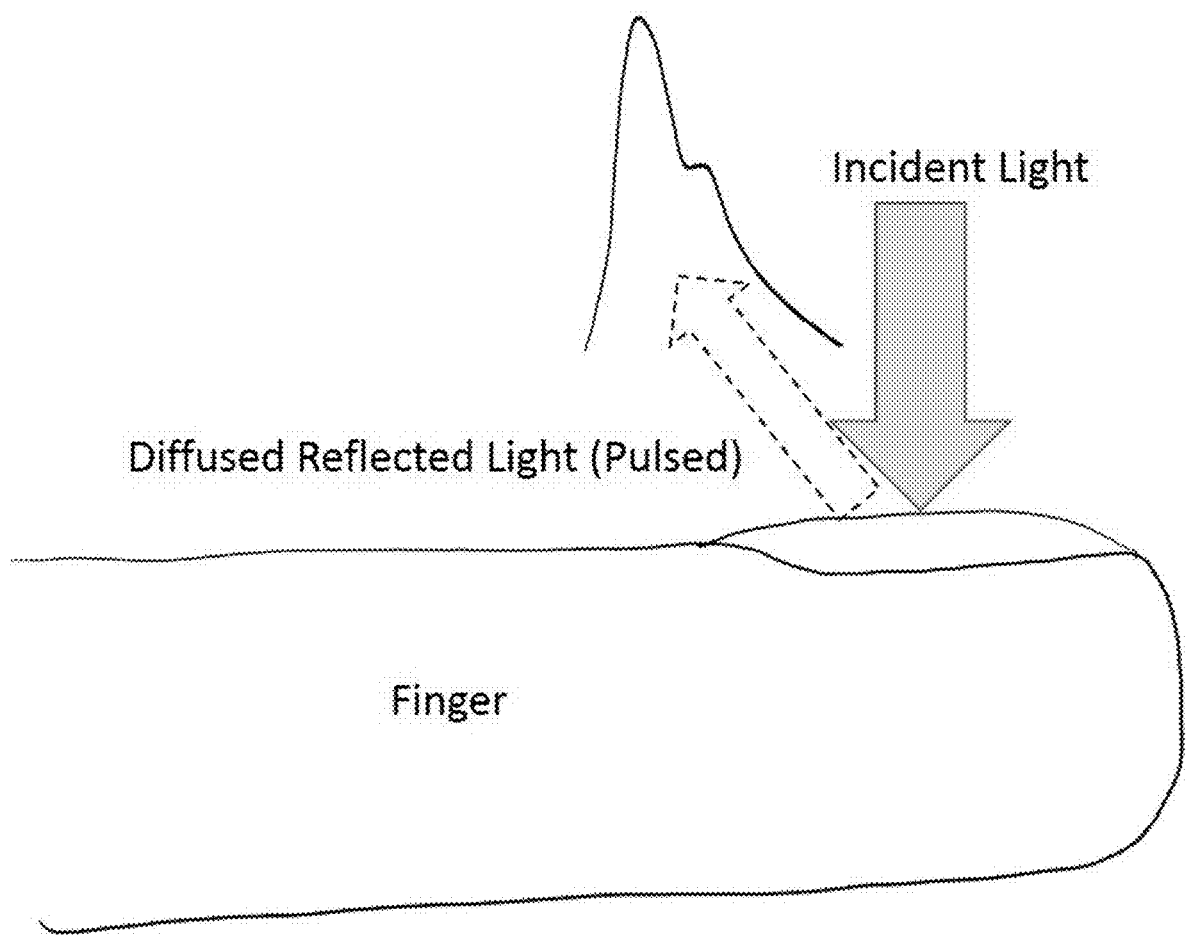
FIG. 4 illustrates the measurement of diffuse reflection of light through a finger.

FIGS. 3 and 4 illustrate two different methods for measuring the level of water in human body. In FIG. 3 the method is based on transmission and in FIG. 4 the method is based on diffuse reflection. In FIG. 3, as an example, continuous radiation projects on a subject's finger, and then the transmitted light, which is modulated due to blood pulsate behavior, is directed to a detector. Then the intensities of the pulsated transmitted light at two different wavelengths, one inside the water absorption band and one outside, are processed and the amplitudes of both signals are compared.

In both diffused reflection and transmission methods, the interference of ambient light could be corrected by applying a reference measurement prior to real measurement. In this reference measurement the probe detectors measure the ambient lights when there is no sample inside the probe. This measurement may be called the dark correction factor. In certain embodiments, the dark correction factor is measured every time prior to measurement of the subject's hydration state.

Furthermore, in transmission methods, the difference of the thickness of a subject's body portion (e.g., a finger) may be taken into account. The thickness parameter should be measured for each subject's body portion prior to real measurement. To obtain the thickness parameter, after a sample is located between the light source and the detector, the level of the transmitted light intensity outside of the water absorption band in measured and then this level is compared with the expected intensity level (for example with the intensity level registered in the device memory). Then the intensity of the light source is modified to bring the transmitted light equal to expected level. This is called device light intensity level normalization. There are a few techniques to normalize a device light intensity and one of them is Pulse Width Modulation ("PWM").

As mentioned above, two important parameters to calibrate the device are level of illumination light intensity and illumination light spectral shape. In some embodiments, the light intensity level is measured before each measurement as part of device calibration. There are a few mechanisms that exist for this calibration. For example, in certain embodiments in which the light source is wideband (e.g., a light bulb), a portion of the illumination light spectrum (a wavelength region), which is not located in the water absorption band and also does not overlap with other tissue chromophores or absorbers absorption bands, or an extra narrow band light source that illuminates outside the water absorption band, can be employed. The intensity of this portion of the illumination light spectrum or the illumination provided by the extra narrow band light source is compared with the device standard, and then the illumination intensity is adjusted. In certain other embodiments in which the illumination light is narrowband (like LEDs), one specific LED for which the emission spectrum does not overlap the water absorption band or other strong chromophore and absorbers is employed. This specific LED is used to calibrate the device based on its intensity level.

For a second calibration, which is an illumination light spectral calibration, one may use a spectral reference. Generally in both transmission and diffuse reflection spectroscopy, the concentration of the desired chemical compound can be measured by comparing the reference light and the diffused reflected or transmitted light. This reference could be either a back-reflected light from a perfect white standard or part of the attenuated illumination light. In this disclosure, this reference signal is called Ref. Thus, to measure the concentration level of a desired compound (e.g., water), the transmitted or diffused reflected light, which is called W, is compared with that reference light. Basically this method is called Beer-Lambert's law. If the device is in reflectivity-based mode, then Beer-Lambert's law can be formulated as:

$$\text{Reflectivity}(\lambda) = (W(\lambda)/\text{Ref}(\lambda)) * 100$$

And then:

$$\text{Absorbance}(\lambda) = -\log(\text{Reflectivity}(\lambda)/100)$$

If the device uses a transmission-based mode, then either a perfect white standard or a portion of the illumination light source could be used as a reference. As an example, in transmission-based mode the device captures the illumination light (either wideband or narrowband) before the measurement. The light spectral shape is memorized by device. Then the device compares the illumination light with the transmitted light to obtain the absorbance of a desired compound. It can be formulated as:

$$\text{Absorbance}(\lambda) = -\log(\text{Illumination Light}(\lambda)/\text{Transmitted Light}(\lambda))$$

In this method, the absorbance obtained from Beer-Lambert' law indicates the stationary or static amount of water in tissue (including blood). The dynamic level of water is obtained from comparing the pulse amplitudes of signals inside and outside of the water absorption band. This feature avoids the interference of any external parameter that makes the water level in blood and tissue surrounding blood vessels inaccurate. One then compares the absorbance between two different wavelengths, one that overlaps with absorption spectra of the water and one outside (which may be called the baseline), and then measures the amplitude of pulses in those two different wavelengths. The equation may be rewritten as:

$$\Delta A_{dynamic} = \text{Pulse Amplitude}(\lambda \text{inside})/\text{Pulse Amplitude}(\lambda \text{outside})$$

Or $$\Delta A_{dynamic} = [\text{Pulse Amplitude}(\lambda \text{inside}) - \text{Pulse Amplitude}(\lambda \text{outside})]/\text{Pulse Amplitude}(\lambda \text{inside})$$

In which "inside" refers to a wavelength region inside the water absorption (e.g. around 970 nm) band and "outside" refers to wavelength region outside the water absorption band (e.g. around 850 nm). $\Delta A$ is proportional to concentration or bioavailability of water in blood and tissues surrounded the blood. In other words, this can be considered as the body hydration level.

It is well-known that one challenge in tissue optics is the effects of unwanted pigments and other compounds in measurement of the compound one wants to measure. As an example, melanin pigment can absorb the light in Vis-NIR region and decreases the signal to noise ratio, resulting in weak signal, or in other words affect the obtained hydration levels. In certain embodiments, the portion of light which absorbed by other pigments like melanin is compensated by adjusting the illumination light levels.

The methods disclosed herein may be used to assess the hydration status of a person over some period of time or during the performance of an activity, such as an athletic event or work in a high-temperature environment. In certain embodiments, a baseline measurement is taken prior to initiation of the activity. During the course of the activity, one or more measurements may be taken and compared to the baseline measurement to determine the impact of the activity on the person's hydration status.

In some embodiments, measurements could be taken at a plurality of timepoints. In certain embodiments, a device could be programmed to take measurements at a plurality of timepoints. In some embodiments, the device might be worn (e.g., on the finger or wrist) during the activity. The timepoints could be periodic, that is, at predetermined time intervals (for example, every five minutes, every ten minutes, once per hour, etc.). Alternatively, the device could be programed to take more frequent measurements if a particular hydration threshold is reached, for example, if the device user's hydration level has declined below a particular level that indicates that the user is dehydrated or at risk of becoming dehydrated. In some embodiments, the device is programmed to emit an audible or visual alarm if a particular predetermined hydration level is reached. In other embodiments, the measurement device may communicate with a second device such as a cellular phone, exercise machine, or computer in a lab or clinic, via a wired or wireless connection.

EXAMPLES

To further illustrate these embodiments, the following examples are provided. These examples are not intended to limit the scope of the claimed invention, which should be determined solely on the basis of the attached claims.

Example 1

As a numerical example, both the stationary and dynamic part of the hydration level for a subject as illustrated in FIG. 2, could be determined here using the equation in equation 3: The difference of the value of any point in pulsated waveform in P1 compared to the corresponding point in waveform P2 is an indication of the stationary part of the hydration level which depends on water availability in tissue, blood and other external parameters discussed above and for this specific example is:

$$\Delta A_{static} = 247 - 207 = 40 (a.u.).$$

The dynamic part of the hydration level is the difference of pulse amplitude of P1 and P2. This gives us only the water availability in blood and adjacent tissue and does not depend on other external parameters as they cannot be pulsated. Here in this example the difference amplitude for waveform P1 and P2 is $$\Delta A_{dynamic} = [247-236] - [203-195] = 3 (a.u.) \text{ or } 27\%$$

Which means in this subject the water availability in plasma is 27%.

Example 2

Figure 5:
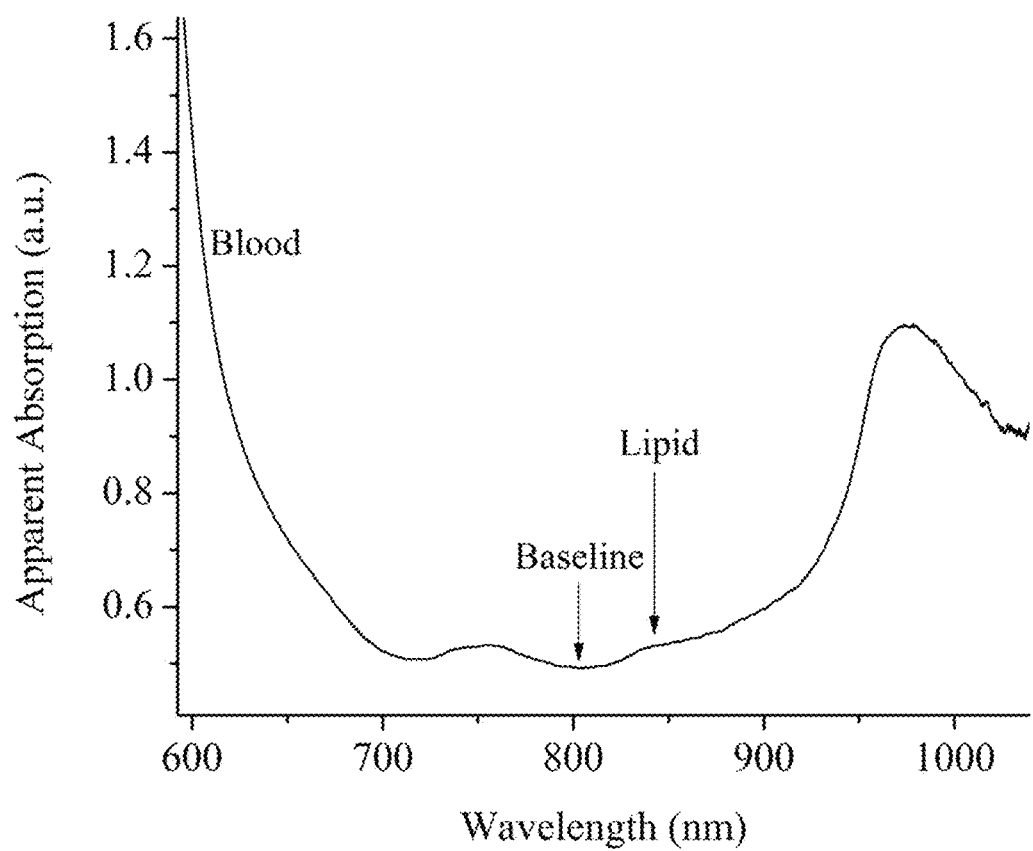
FIG. 5 is an absorption spectrum through a human index finger in which the lipid absorption band is indicated.

In another example, one could measure the amount of the lipid in the blood and blood-surrounded tissue. In this case, two signals, one inside the lipids absorption band, e.g., 850 nm, and one outside the lipid absorption band, e.g., 800 nm, are compared, and the difference between signal amplitudes can indicate the level of lipid in the blood. See FIG. 5.

Example 3

Figure 6:
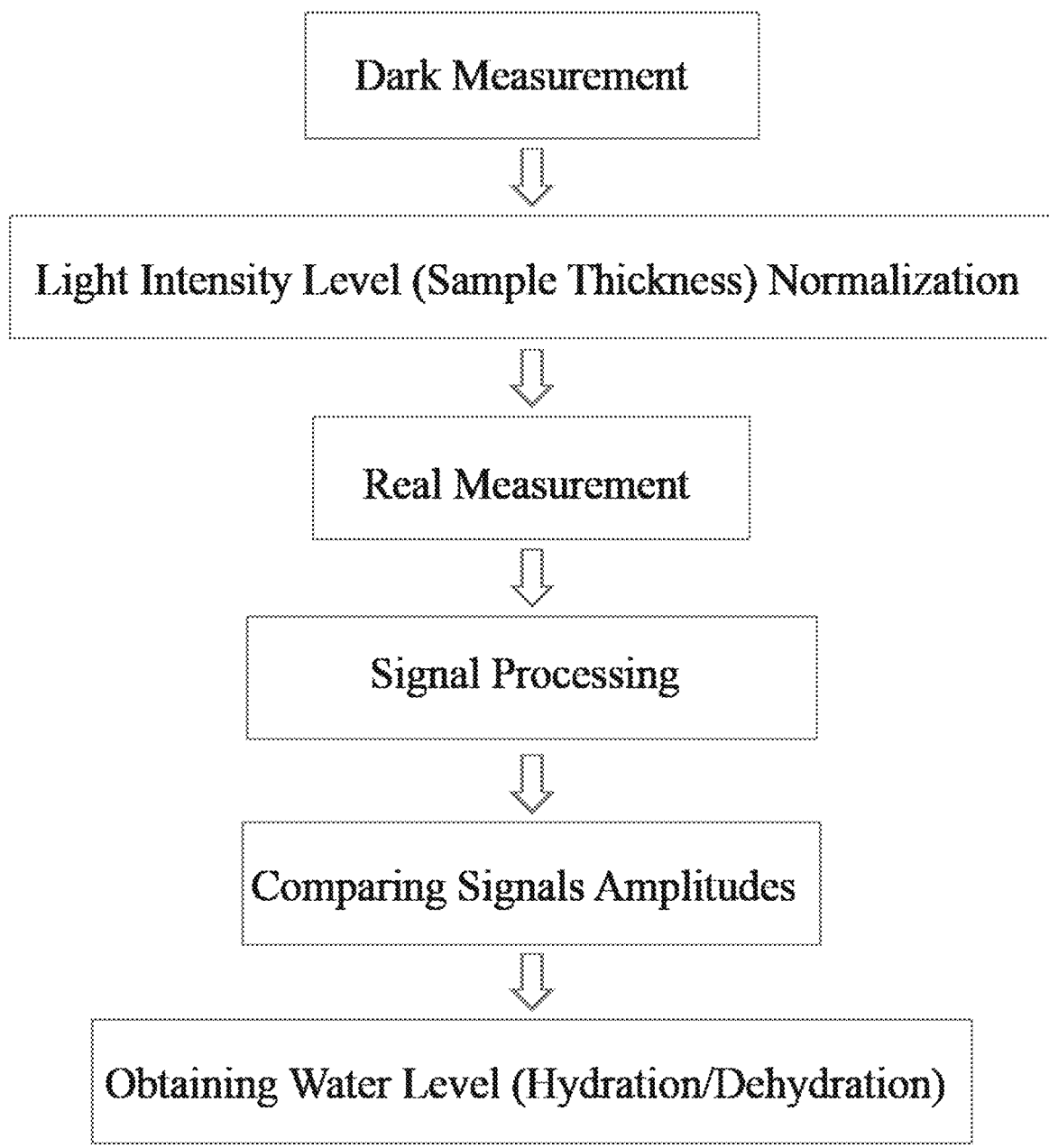
FIG. 6 illustrates an algorithm to collect and process data and obtain a hydration level.

In another example, the algorithm to collect and process the data and obtain the hydration level is demonstrated in FIG. 6. At the first step, the device measures the dark spectrum to subtract it from all real measurements. This dark spectrum in fact is a mixture of all electrical or optical noises. The dark spectrum is saved in the instrument memory to be subtracted from any real hydration measurement. The next step is light illumination normalization. In this step the sample thickness and all tissue characteristics which might interfere with the real measurement are measured and, based on this measurement, the illumination light will be adjusted. Then in the "real measurement" step, the data acquisition is performed and the signal is collected continuously until the blood waveform is established in the device. Next, the signals are processed and by comparing signals amplitudes in two wavelength regions, the hydration level in blood and surrounding tissue is obtained as illustrated in the last step.

Example 4

Figure 7:
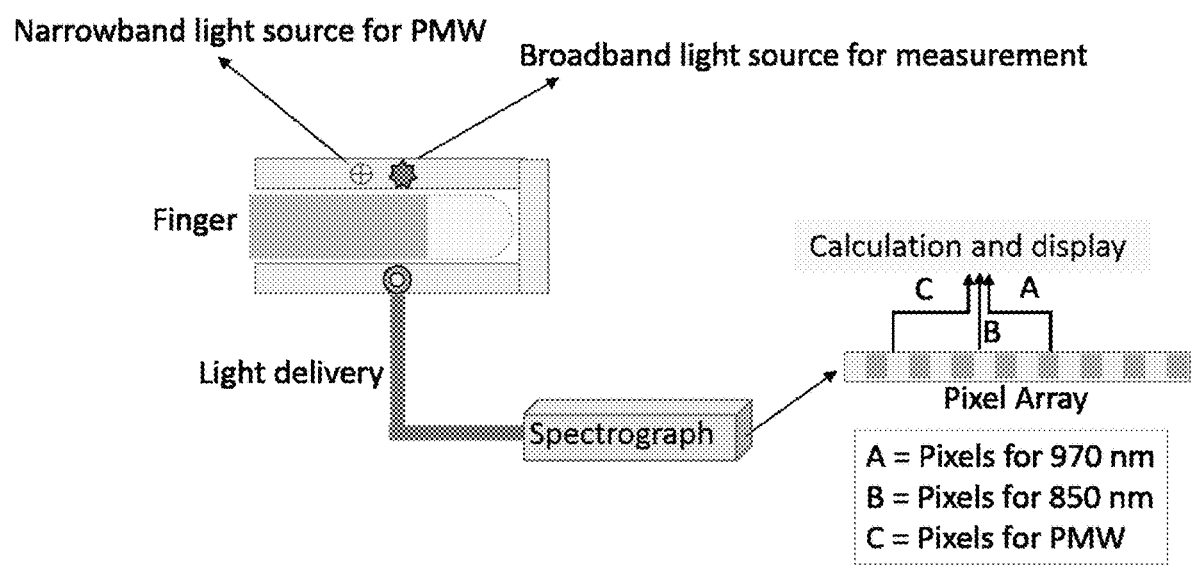
FIG. 7 illustrates a schematic of one prototype for measuring a person's hydration level.

A schematic of one prototype is illustrated in FIG. 7. The device comprises a broadband light source which covers at least two wavelengths: one that overlaps the absorption band of water (here 970 nm) and a second that lies outside the absorption band of water (here 850 nm). The device shown also comprises an independent narrowband light source that emits at a wavelength that is located outside of the absorption band of the water (nearly 850 nm). This narrowband light source is used to compensate for different tissue characteristics, e.g. finger thickness and skin, and by using the PWM method to adjust the broadband light source intensity to an appropriate level.

The device further comprises an aperture for the subject's finger. The light from the light sources that pass through the subject's finger are collected by a spectrograph. The data generated by the spectrograph are transmitted to the device's hardware to be analyzed, and the result is displayed on a monitor.

Example 5

Figure 8:
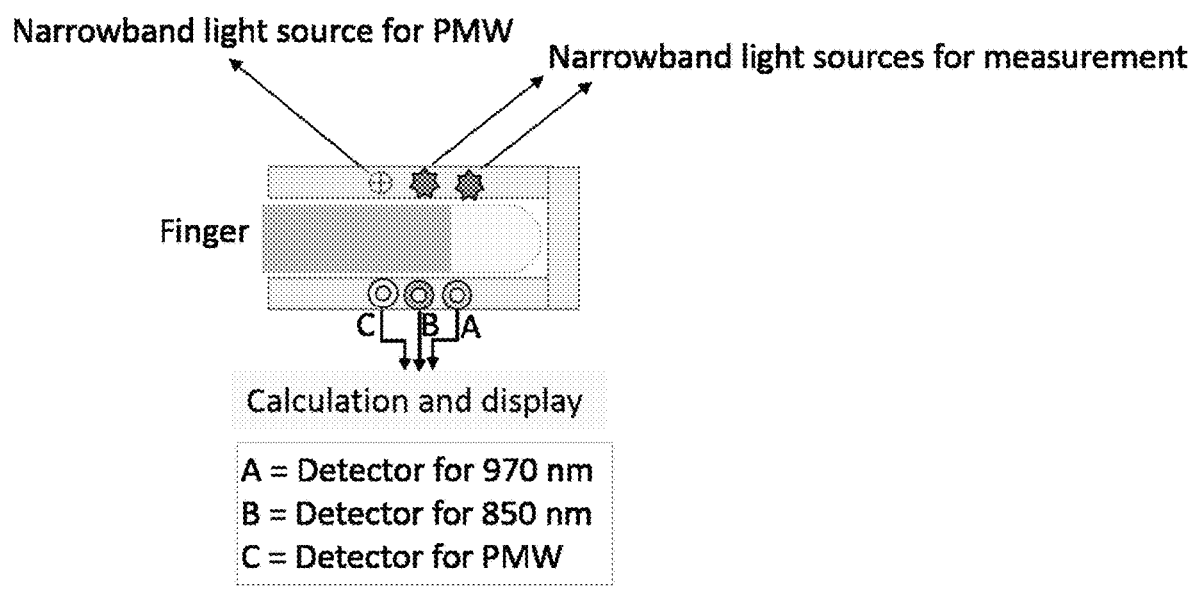
FIG. 8 schematically illustrates a miniaturized device for measuring a person's hydration level.

A miniaturized version of the device described in Example 4 is illustrated in FIG. 8. Instead of a broadband light source, this device comprises two different narrowband light sources. The wavelength of one of the light sources is located inside the water absorption band (970 nm) and the wavelength of the second narrowband light source is located outside the water absorption band. In both devices, the data is analyzed by the hardware and displayed in the monitor.

Example 6

A device (similar to that described in Example 5) could be worn by a person (e.g., on the finger or wrist) and used to collect data from the person during the performance of an activity, such as an athletic event or work in a high-temperature environment, at a plurality of timepoints, including a baseline measurement prior to initiation of the activity. The device is programmed to take measurements at specific periodic timepoints (e.g., every five minutes) and compare those measurements to the baseline measurement. If the comparison suggests that the person's hydration level has declined below a particular threshold, the device is programmed to emit an audible or visual alarm.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A device for measuring a hydration level of a subject comprising:
    at least one light source that emits a first wavelength of light and a second wavelength of light, wherein the first wavelength of light overlaps an absorption band of water and the second wavelength of light lies outside the absorption band of water;
    a detector for measuring intensity of light at the first wavelength and the second wavelength over a period of time that corresponds with a blood flow pulse of a body portion of the subject;
    an aperture for the body portion of the subject, wherein when the body portion is inserted into the aperture, the detector measures intensity of light through the body portion at the first wavelength over the period of time to form a first waveform and intensity of light through the body portion at the second wavelength over the period of time to form a second waveform;
    a computing portion that compares a first amplitude of the first waveform and a second amplitude of the second waveform to determine the hydration level of the subject, wherein the first waveform and the second waveform each have a peak and a trough, the first amplitude is measured from the peak of the first waveform to the trough of the first waveform and the second amplitude is measured from the peak of the second waveform to the trough of the second waveform; and an output portion to display the hydration level.

2. The device of claim 1, wherein the subject is a human.

3. The device of claim 2, wherein the body portion is a finger.

4. The device of claim 2, wherein the body portion is a wrist.

5. The device of claim 1, wherein the first wavelength of light is one of approximately 970 nm, approximately 1200 nm, approximately 1450 nm, or approximately 1950 nm.

6. The device of claim 5, wherein the first wavelength of light is approximately 970 nm and the second wavelength is approximately 800 nm.

7. The device of claim 1, wherein the detector comprises a spectrometer.

8. The device of claim 1, wherein the detector comprises an array of sensors.

9. The device of claim 1, wherein the light source comprises a wideband emitter.

10. The device of claim 1, wherein the light source comprises a plurality of narrow band emitters.

\* \* \* \* \*